United States Patent [19]

Jessel, Jr. et al.

[11] Plant 4,206

[45] Feb. 7, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 765,431

[22] Filed: Feb. 4, 1977

[51] Int. Cl.[2] ..... A01H 5/00

[52] U.S. Cl. ..... Plt./75

[58] Field of Search ..... Plt./75, 77

*Primary Examiner*—Robert E. Bagwill
*Attorney, Agent, or Firm*—Donald D. Jeffery

[57] ABSTRACT

A novel chrysanthemum of the pompon type characterized by white ray florets and tolerance of frost.

1 Drawing Figure

1

The present invention comprises a new and distinct cultivar of *Chrysanthemum morifolium*, Ramat., hereinafter referred by the cultivar name Popcorn (#74074003).

Popcorn is a product of a planned breeding program which had the objective of creating cultivars with pompon capitulum type, short height, spreading branching pattern, durable inflorescence, short (6 to 7 week) flowering response period, and white ray floret color under outdoor natural season conditions.

Popcorn was originated from a cross made in a controlled breeding program in Barberton, Ohio in the year 1973. The male parent was 128/72 (#21720E33; unnamed seedling), a white decorative. The female parent was Pearls (#73007M03; U.S. Plant Pat. No. 3,970), a white pompon.

Popcorn was discovered and selected as a flowering plant within the progeny of the stated cross by Walter H. Jessel, Jr. on May 4, 1974 in an outdoor field in Ft. Myers, Fla.

The first act of asexual reproduction of Popcorn was accomplished when vegetative cuttings were taken from the initial selection in July, 1974, in a controlled environment in Barberton, Ohio by a technician working under formulations established and supervised by William E. Duffett and Walter H. Jessel, Jr. Horticultural examination of selected units initiated Oct. 8, 1974 has demonstrated that the combination of characteristics as herein disclosed for Popcorn are firmly fixed and are retained through successive generations of asexual reproduction.

Popcorn has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatological Data, Annual Summary With Comparative Data*, Akron, Ohio, U.S. Department of Commerce, National Oceanic and Atmospheric Administration, Environmental Data Service, Washington, D.C. 1974, 1975, 1976, and *Tables of Sunrise, Sunset, and Twilight.* Supplement to the American Emphermeris, 1946., U.S. Naval Observatory, Washington, D.C., pg. 103.

The following traits have been repeatedly observed and are determined to be basic characteristics of Popcorn which in combination distinguish this chrysanthemum as a new and distinct cultivar:

2

1. Flat capitulum form, reflexing at maturity.
2. Pompon capitulum type.
3. White ray floret color tinging pink with finishing temperatures below 56° F.
4. Diameter across face of capitulum up to 50 mm.
5. Permanence of inflorescence ranging from 14 to 21 days.
6. Medium plant height (requiring 1–2 long day weeks prior to short days and 1 application of 2500 ppm B9-SP to attain a flowered plant height of 30 to 35 cm.).
7. Spreading branching pattern.
8. Good tolerance of inflorescence to frost damage.
9. Average natural season flowering date of September 25.
10. Average flowering response period of 7 weeks in photoperiodic controlled flowering programs.

The accompanying photographic drawings show typical inflorescence and foliage characteristics of Popcorn. Sheet 1 is a color photograph of Popcorn. Sheet 2 is a black and white photograph showing three views of the inflorescence of Popcorn. Sheet 3 is a black and white photograph showing the foliage of Popcorn at three stages of growth.

Of the many commercially available cultivars known to the present inventors, the most similar existing cultivars in comparison to Popcorn are Baby Tears (#21680E05; unpatented) and Pearls. Reference is made to attached Chart A which compares certain characteristics of Popcorn with the same characteristics of the above identified cultivars. General comparisons are as follow:

1. In comparison to Baby Tears, Popcorn has different ray floret color, later average natural season flower date, taller plant height, and larger diameter across face of capitulum. The capitulum form, capitulum type, branching habit, and plant spread of Baby Tears are similar to those of Popcorn.

2. In comparison to Pearls, Popcorn has an earlier average natural season flower date, shorter plant height, more spreading branching pattern, and larger diameter across face of capitulum. The capitulum form, capitulum type and ray floret color of Pearls are similar to those of Popcorn.

In the following description, color references are made to The Munsell Limit Color Cascade, 1972 edition. The color values were determined between 9:30 and 10:00 A.M. on Oct. 4, 1976 under 120 foot-candle light intensity at Barberton, Ohio.

Botanical classification: *Chrysanthemum morifolium,* Ramat., cv Popcorn.

INFLORESCENCE

Capitulum:

*Form.*—Flat.

*Type.*—Pompon (commercial double).

*Permanence.*—14–21 days.

*Diameter across face.*—37 to 50 mm.

Corolla of ray floret:

*Color (abaxial).*—26-2 (immature) to white.

*Color (adaxial).*—26-1 to white.

Reproductive organs:

*Androecium.*—Present disc florets; scant pollen.

*Gynoecium.*—Present both ray and disc florets.

PLANT

General appearance: spreading; medium height.

Duration and texture: herbaceous; perennial.

Foliage:

*Color (abaxial).*—Between 22–13 and 22–14.

*Color (adaxial).*—22-12 overcast with white.

CHART A
COMPARISON OF POPCORN, BABY TEARS AND PEARLS

| CULTIVAR | RAY FLORET COLOR | CAPITULUM FORM AND TYPE | AVERAGE NATURAL SEASON FLOWER DATE | PLANT HEIGHT | BRANCHING PATTERN AND SPREAD | DIAMETER ACROSS FACE OF CAPITULUM |
|---|---|---|---|---|---|---|
| Popcorn | White | Flat Pompon | September 25 | Medium, from 30 to 35 cm. | Spreading from 35 to 40 cm | 37 to 50 mm. |
| Baby Tears | Ivory White | Flat Pompon | September 20 | Short, from 20 to 25 cm. | Spreading, from 35 to 40 cm | 25 mm. |
| Pearls | White | Flat Pompon | October 1 | Tall, from 35 to 40 cm. | Semi-spreading, from 30 to 35 cm. | 25 mm. |

COMPARISONS MADE OF PLANTS GROWN UNDER NATURAL SEASON OUTDOOR FIELD CONDITIONS IN BARBERTON, OHIO

We claim:

1. A new and distinct cultivar of *Chrysanthemum morifolium,* Ramat. known by the cultivar name Popcorn and characterized particularly as to uniqueness by the combined characteristics of flat capitulum form, reflexing at maturity; pompon capitulum type; white ray floret color, tinging pink with finishing temperatures below 56° F; diameter across face of capitulum up to 50 mm; permanence of inflorescence ranging from 14 to 21 days;medium plant height; spreading branching pattern; good tolerance of inflorescence to frost damage; average natural season flowering date of September 25; and average flowering response of 7 weeks in photoperiodic controlled flowering programs.

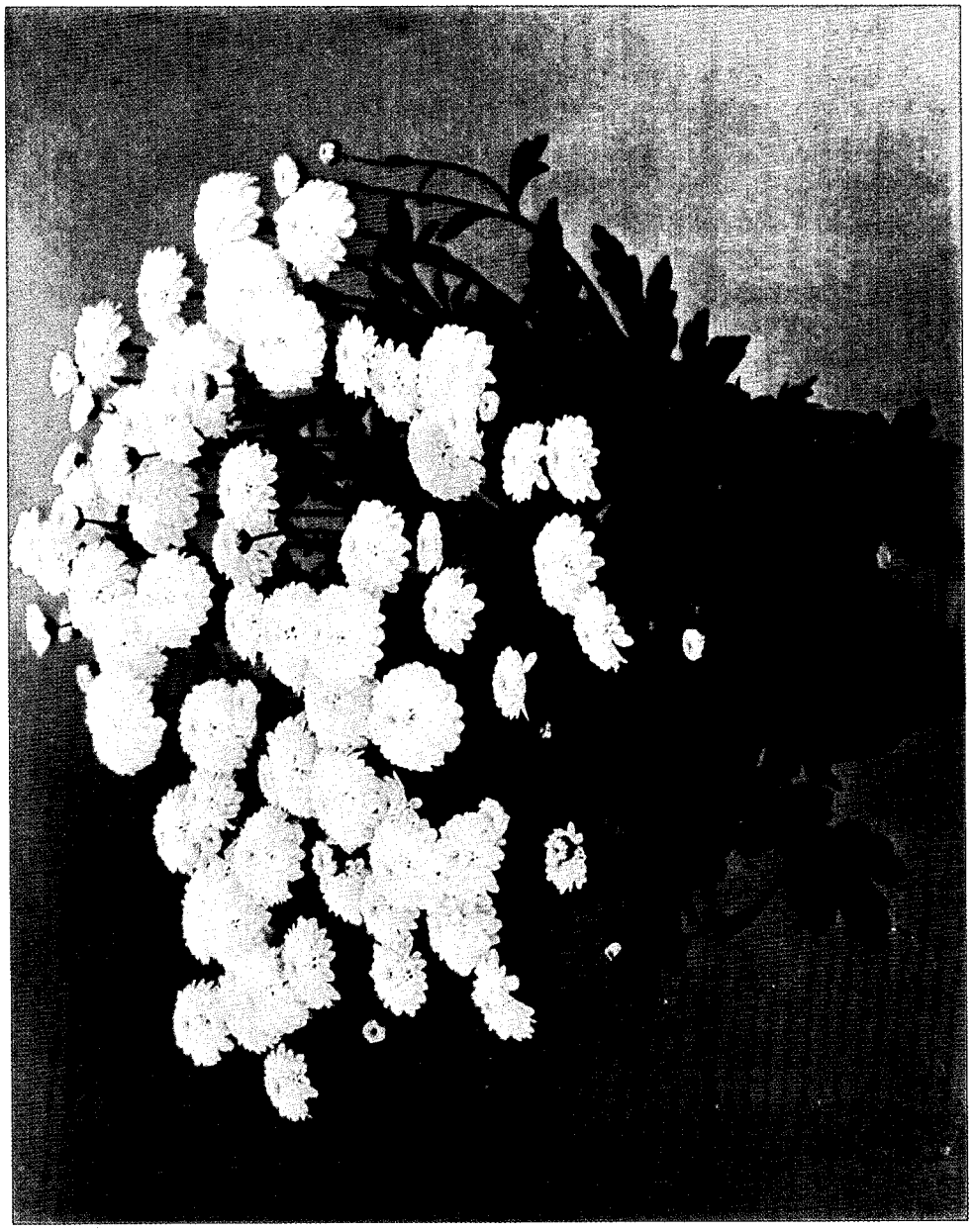

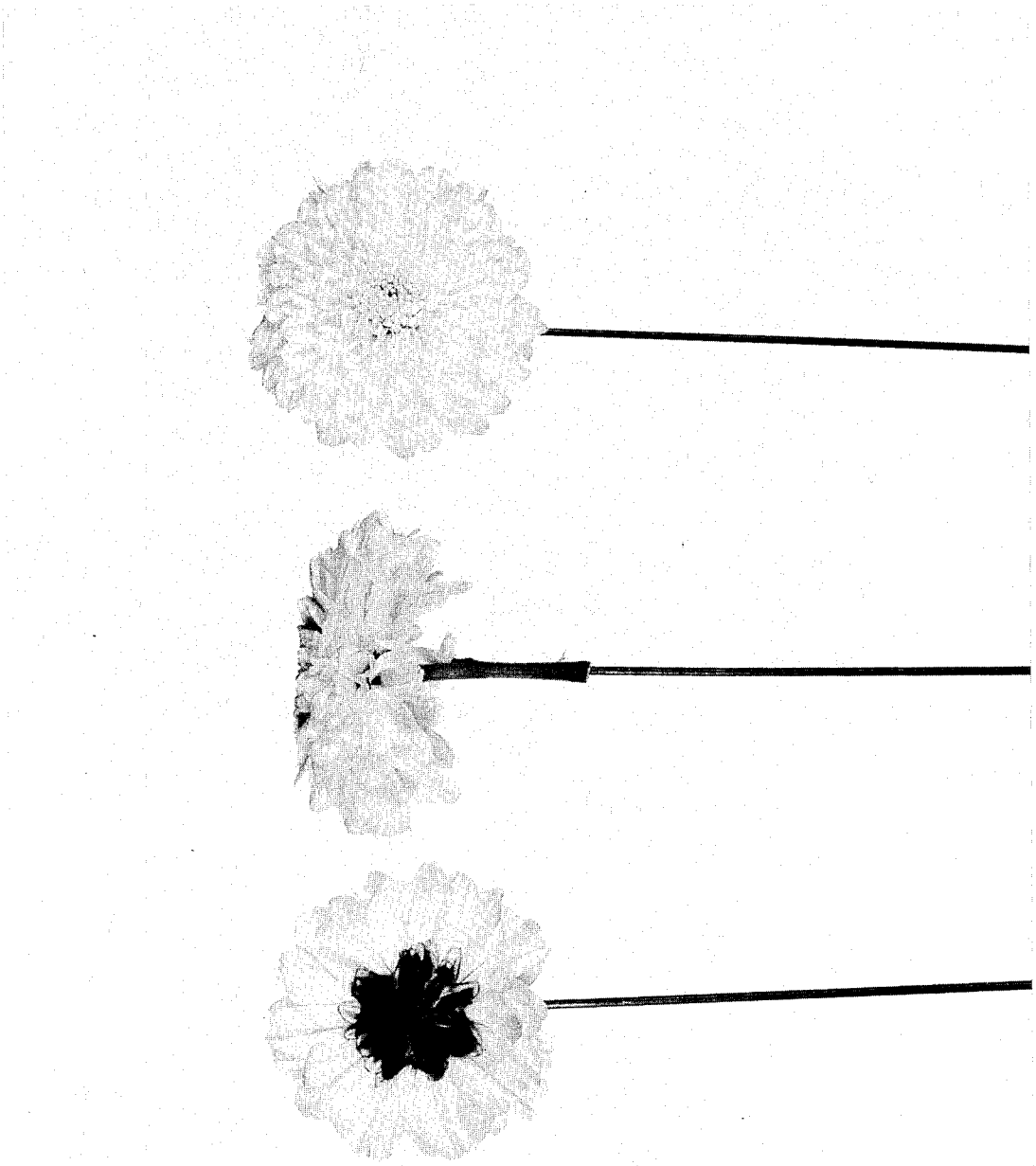

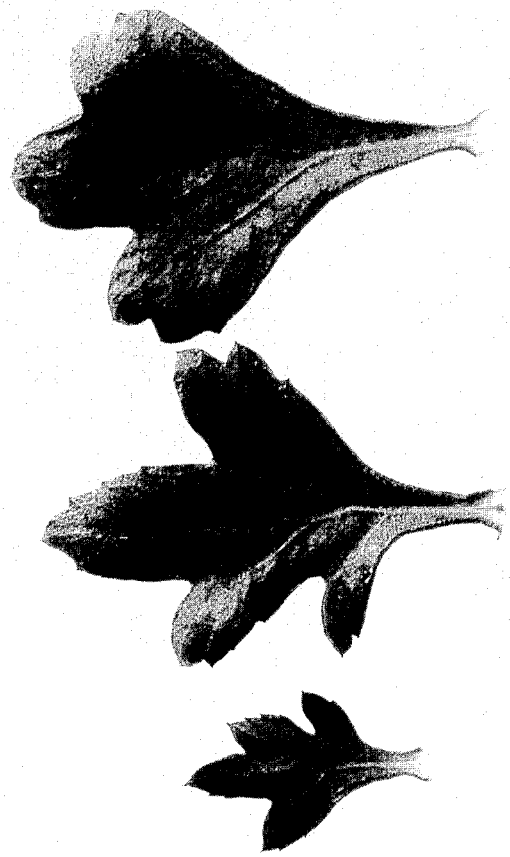

* * * * *